United States Patent [19]

Webster, II

[11] Patent Number: 4,834,085

[45] Date of Patent: May 30, 1989

[54] PERSON-TO-PERSON RESUSCITATION DEVICE

[76] Inventor: John W. Webster, II, 1529 N. Park St., Apt. 1, Indianapolis, Ind. 46202

[21] Appl. No.: 130,987

[22] Filed: Dec. 10, 1987

[51] Int. Cl.⁴ .......................................... A61M 16/00
[52] U.S. Cl. ........................... 128/203.11; 128/202.29
[58] Field of Search ................... 128/202.28, 202.29, 128/203.11, 206.26

[56] References Cited

U.S. PATENT DOCUMENTS

| | | | |
|---|---|---|---|
| 938,247 | 10/1909 | Kuhn | 128/206.26 |
| 1,105,127 | 7/1914 | Dräger | 128/206.26 |
| 1,244,661 | 10/1917 | Teter | 128/206.26 |
| 2,666,432 | 1/1954 | Stanton | 128/206.26 |
| 3,905,361 | 9/1975 | Hewson et al. | 128/202.28 |
| 4,497,318 | 2/1985 | Donmichael | 128/202.28 |

FOREIGN PATENT DOCUMENTS

| | | | |
|---|---|---|---|
| 775911 | 5/1957 | United Kingdom | 128/206.26 |
| 185017 | 5/1907 | Fed. Rep. of Germany | 128/206.26 |
| 643948 | 4/1937 | Fed. Rep. of Germany | 128/206.26 |
| 294515 | 1/1954 | Switzerland | 128/206.26 |

OTHER PUBLICATIONS

Intertech Brochure No. B8701 (4/87) 15M on Safe Response ™ Mouth-to-Mouth Mask, from Intertech Resources, Inc., 2275 Half Day Road, Suite 175, Bannockburn, Il. 60015.
Laerdal Pocket Mask ™ Brochure, Armstrong Medical Industries, Inc., 3660 Commercial Ave., P.O. Box 7, Northbrook, Il 60065.
Catalogue #111, Armstrong Medical Industries Inc., 3660 Commercial Ave., P.O. Box 7, Northbrook, Il. 60065, p. 18.
Keller Medical Specialties Catalogue, Keller Med. Spec., 42609 Crawford Road, Antioch, Il. 60002, pp. 1-4.

Primary Examiner—Edgar S. Burr
Assistant Examiner—Aaron J. Lewis
Attorney, Agent, or Firm—Carl A. Forest

[57] ABSTRACT

An inflatable, cone-shaped mask is attached to one end of a hollow housing and a mouthpiece is attached to the other. A valve in the housing is switchable between two positions. In one position it directs breath from an active breather blowing in the mouthpiece into the mask to inflate it. In the second position it directs the breath through the mask, which may be sealably engaged about the nose and mouth of a passive breather to be resuscitated. A second valve in the housing prevents fluid from passing from the mask to the mouthpiece. A spin separator trap separates moisture from the breath of the active breather as it passes through the housing. A second spin separator trap prevents moisture that may leak from the first trap from falling into the breathing organs of the passive breather. A screen in the housing prevents regurgitation from the passive breather from entering the second valve chamber. When not inflated, the mask is foldable back over the housing. The entire device is sufficiently compact to fit in an ordinary-sized clothes pocket.

7 Claims, 3 Drawing Sheets

4,834,085

PERSON-TO-PERSON RESUSCITATION DEVICE

BACKGROUND OF THE INVENTION

1. Field of the Invention

The invention in general relates to person-to-person resuscitation devices, and more particularly to such a resuscitation device that protects both the passive and active breather from exchange of bodily fluids which may carry disease and at the same time is so compact that it can easily be carried in an ordinary-sized clothes pocket.

2. Description of the Prior Art

Devices to facilitate "mouth-to-mouth" resuscitation have been well-known for more than thirty years and are widely used by nurses, emergency personnel, physicians and the general public, particularly since cardiac-pulmonary respiration (CPR) has become widely taught. Such resuscitation devices are sometimes referred to as mouth-to-mouth resuscitation devices, however this phraseology is not accurate since the device usually covers the patient's nose as well as mouth. We shall refer to them herein as person-to-person resuscitation devices, which is not only accurate, but also serves to distinguish the devices from mechanical resuscitation devices which involve a different set of problems and constraints. The person-to-person resuscitation devices are also sometimes called ventilation masks. Numerous ventilation masks have been developed. Most include a mouthpiece or other means for receiving the rescuer's or active breather's breath, a face mask or other means for applying the breath to the patient or passive breather, and a one-way valve connecting the mouthpiece and the mask. The device is used by placing the face mask about the patient's nose and mouth and blowing through the mouthpiece. All of the ventilation masks prevent mouth-to-mouth contact between rescuer and patient. Most are transparent to permit the rescuer to watch for patient lip color, regurgitation, etc. Other features found in prior art ventilation masks include cone-shaped, rigid plastic mask structures, inflatable, donut-shaped bladders about the large end of the cone for forming a seal between the patient and the mask about the breathing organs of the patient, and ported valves which permit the patient to exhale even when the mouthpiece is closed by the rescuer's mouth.

One goal of ventilation mask designers has been small size, since the smaller the mask, the easier it is to carry and thus have it readily available in emergencies. Some of the ventilation masks are relatively small, although, until now, none have yet been small enough to be easily carried in an ordinary-sized clothes pocket.

Another goal of ventilation mask designers has been to reduce the possibility of the exchange of bodily fluids in order to prevent the transmission of disease. To this end, features designed into ventilation masks have included one-way valves which permit the active breather's breath to pass to the passive breather and prevent the passive breather's breath or other fluid from passing back to the active breather and vents which vent the passive breather's breath away from the active breather's face. However such face masks have invariably also been relatively large and difficult to assemble, which is a significant disadvantage in an emergency situation.

SUMMARY OF THE INVENTION

It is an object of the invention to provide a person-to-person resuscitation device that overcomes one or more of the disadvantages of the prior art devices.

It is another object of the invention to provide a person-to-person resuscitation device that not only protects the active breather from bodily fluids of the passive breather, but also protects the passive breather from the more dangerous of the bodily fluids of the active breather.

It is another object of the invention to provide a person-to-person resuscitation device that prevents regurgitation from the patient from entering the valve chamber.

It is yet another object of the invention to provide a person-to-person resuscitation device that includes a spin separator trap between the active breather and the patient.

It is a further object of the invention to provide a person-to-person resuscitation device that can be carried in an ordinary-sized clothes pocket.

It is yet another object of the invention to provide one or more of the above objects in a person-to-person resuscitation device in which the means for guiding the breath from the valve-sized housing to an area sufficient to cover the passive breather's mouth and nose is inflatable. It is another object of the invention to provide the above object in a person-to-person resuscitation device in which the inflatable means is inflatable through the mouthpiece.

It is still a further object of the invention to provide one or more of the above objects in a person-to-person resuscitation device in which the inflatable means folds back compactly over the housing when not inflated.

The invention provides a person-to-person resuscitation device comprising: means for receiving breath from an active breather; means for applying the breath to a passive breather, valve means for permitting breath to pass from the means for receiving to the means for applying and for preventing fluid from passing from the means for applying to the means for receiving; the means for applying having an opening therein and including an inflatable means for sealably engaging the opening to one or more breathing organs of the passive breather; and the device further comprising a switchable means switchable from a first position to a second position for directing the breath to inflate the inflatable means when in the first position and for directing the breath through the opening in the second position. Preferably the switchable means is part of the means for applying. Preferably the inflatable means comprises a flexible bladder attached to a relatively rigid collar, the bladder and the collar substantially encircling the opening and the collar having at least one inflation port in it. Preferably the switchable means comprises means for closing the one or more inflation ports when the switchable means is in the second position. Preferably the means for closing includes means for applying a bias force to close the one or more inflation ports. Preferably the collar comprises a resilient material and the means for applying a bias force comprises a first hollow cylindrical member and a second hollow cylindrical member, the cylindrical members nested together so that the outer circumference of one cylindrical member abuts the inner circumference of the other cylindrical member, a contact member connected to the first cylindrical member, in contact with the collar, and engageable with the ports, the second cylindrical member attached to the collar and having a lip extending over the rim of the first cylindrical member opposite the collar, and the relative distances between the collar and the lip and the collar and the rim of the first cylindrical member being such that the lip presses against the rim and forces the contact member to compress the collar to provide the bias force.

In another aspect the invention provides a person-to-person resuscitation device comprising: means for receiving breath from an active breather; means for applying the breath to one or more breathing organs of a passive breather; valve means for permitting the breath to pass from the means for receiving to the means for applying and for preventing fluid from passing from the means for applying to the means for receiving., a spin separator trap for trapping moisture in the breath from the active breather; and means for preventing the moisture from dropping from the spin separator trap into the breathing organs of the passive breather.

In a further aspect the invention provides a person-to-person resuscitation device comprising: means for receiving breath from an active breather, means for applying the breath to one or more breathing organs of a passive breather; valve means for permitting the breath to pass from the means for receiving to the means for applying and for preventing fluid from passing from the means for applying to the means for receiving., the device including a valve-sized housing and the means for applying including means for guiding the breath from the valve-sized housing to a larger area sufficient to cover the one or more breathing organs of the passive breather, the means for guiding being inflatable. Preferably the inflatable means for guiding is foldable back over the housing thereby permitting the inflatable means to be compactly arranged about the housing when not inflated.

In yet a further aspect the invention provides a person-to-person resuscitation device comprising: means for receiving breath from an active breather; means for applying the breath to a passive breather; a valve chamber between the means for receiving and the means for applying; a valve member movable in the valve chamber for permitting breath to pass from the means for receiving to the means for applying and for preventing fluid from passing from the means for applying to the means for receiving; and means for preventing regurgitation from the passive breather from entering the valve chamber. Preferably the means for preventing comprises a screen.

The invention provides a person-to-person resuscitation device that is sophisticated as compared to prior art devices relative to its ability to prevent transmittal of disease from the patient to the rescuer and also from the rescuer to the patient. At the same time it is remarkably more compact than prior art resuscitation devices. Numerous other features, objects and advantages of the invention will become apparent from the following detailed description when read in conjunction with the accompanying drawings.

DESCRIPTION OF THE PREFERRED EMBODIMENT

Figure 1:
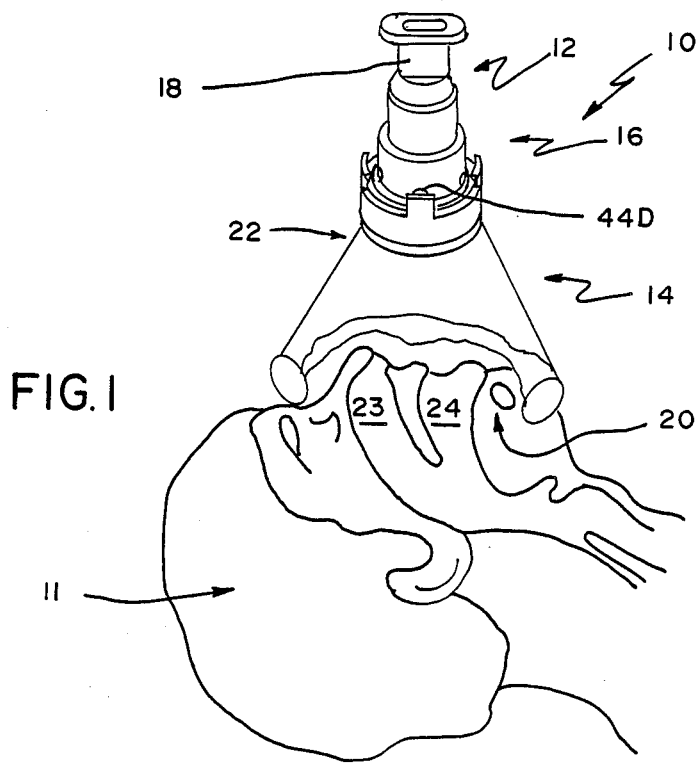
FIG. 1 is a partially cut away view of the resuscitation device according to the invention in position over the mouth and nose of a patient.
Figure 5:
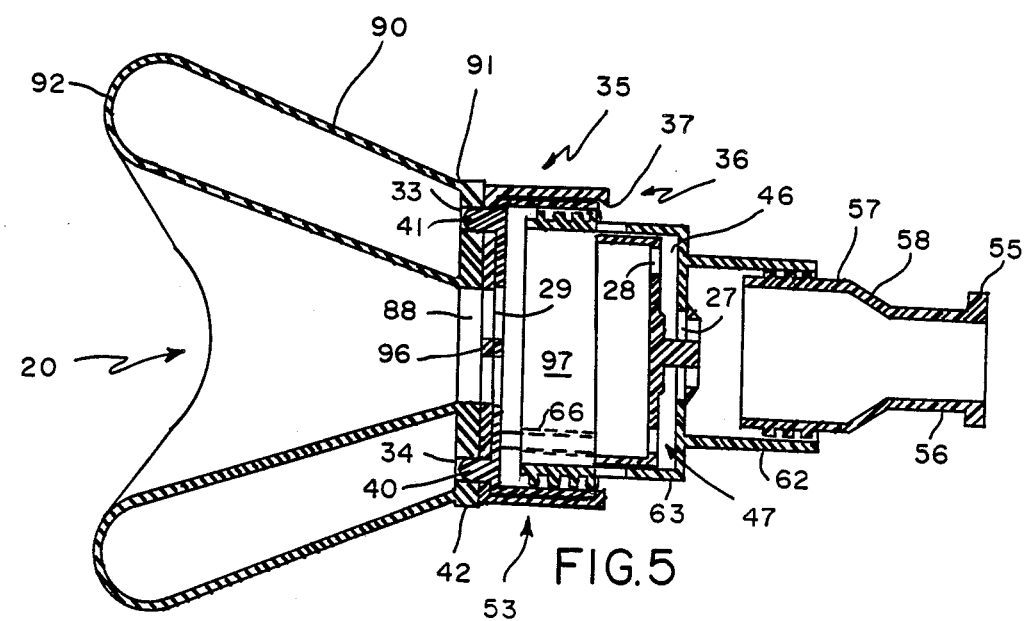
FIG. 5 shows the same cross-sectional view of the invention as in FIG. 2 with the bladder inflated, the switchable valve in the resuscitation position, and the one-way valve in the ventilation position.

Directing attention to FIG. 1, the preferred embodiment of the person-to-person resuscitation device 10 according to the invention is shown in place over the breathing organs of a passive breather 11. It should be understood that the particular device described is exemplary of the invention, and is not intended to limit the invention. The preferred device includes means 12 for receiving breath from an active breather, means 14 for applying the breath to the passive breather, and valve means 16 for permitting the breath to pass from means 12 to means 14 and for preventing fluid from passing from means 14 back to means 12. The means 12 for receiving comprises a mouthpiece 18. The means 14 for applying includes an opening 20 and an inflatable means 22 for sealably engaging the opening 20 to one or more breathing organs 23, 24 of the passive breather. The valve means 16 includes a valve member 26 (FIG. 2) movable within a valve chamber 46 between an open position (FIGS. 2 and 5) in which breath can move through openings 27, 28, 29, and 20 into the nose 23 and mouth 24 of the passive breather 11 and a closed position (FIG. 6) in which shoulder 30 of member 26 seals opening 27 to prevent fluid from passing from the means 14 for applying to the means 12 for receiving.

Figure 2:
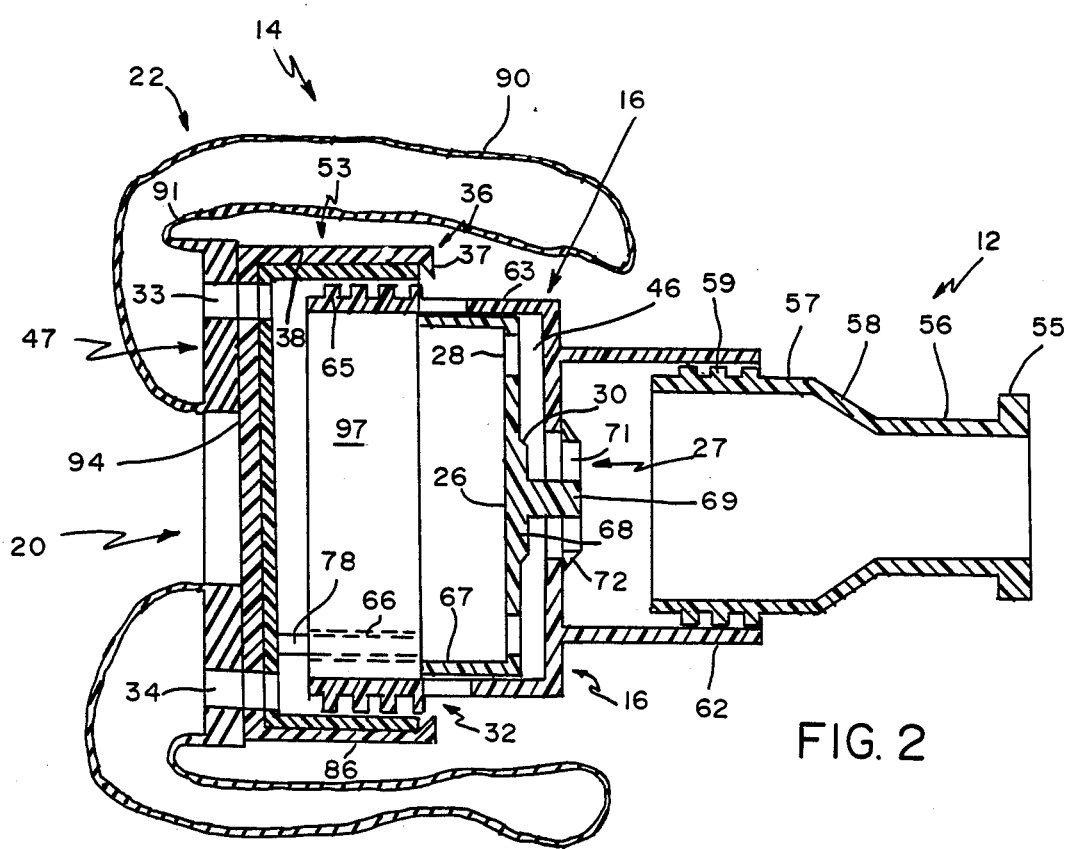
FIG. 2 is a cross section of the device of claim 1 with the bladder not inflated and folded back over the housing and the switchable valve mechanism in the inflation position.
Figure 3:
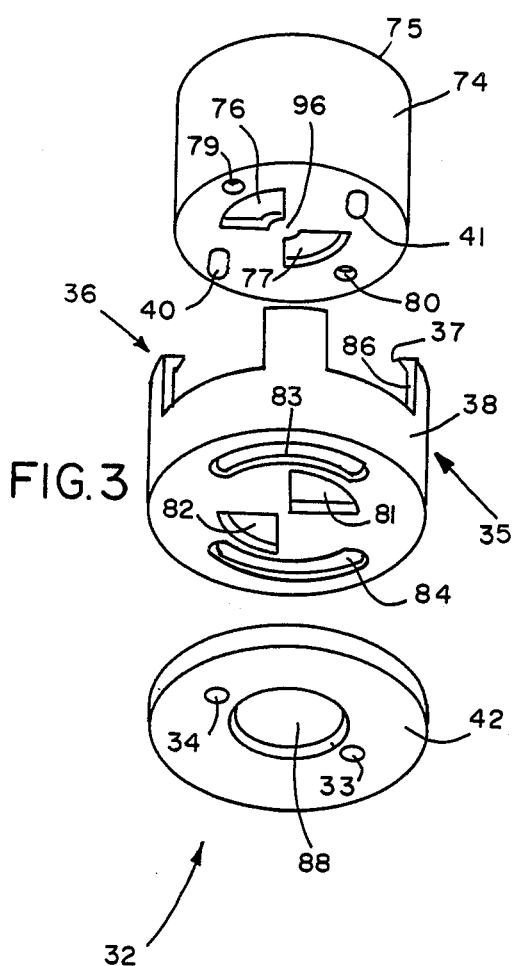
FIG. 3 is an exploded view of the switchable valve mechanism showing the relative rotational positions of the two cylindrical members and the collar in the inflation position.
Figure 4:
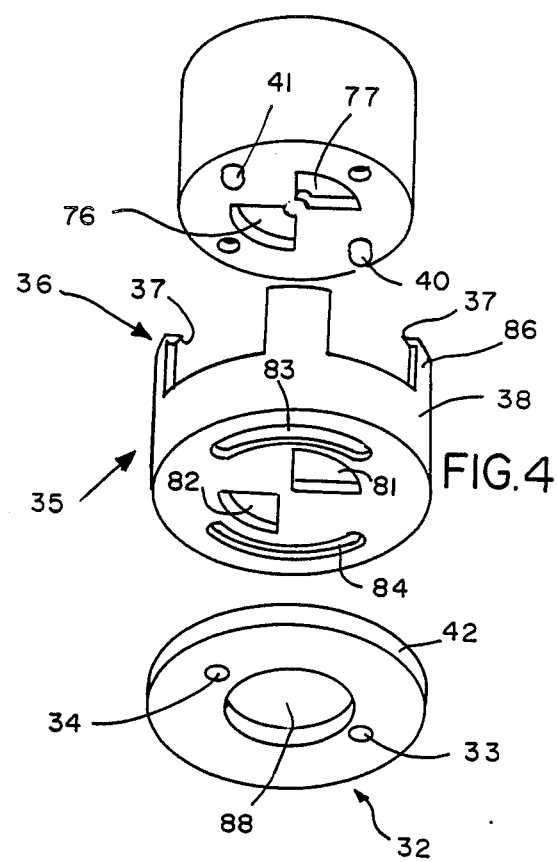
FIG. 4 shows the view of FIG. 3 with the upper cylindrical member rotated to the resuscitation position.

An important aspect of the invention is a switchable means 32 which is switchable from a first position (FIGS. 2 and 3) in which it directs breath through inflation ports 33 and 34 to inflate the inflatable means 22 and a second position (FIGS. 4 and 5) in which it directs the breath through opening 20. The switchable means 32 is best seen in FIGS. 3 and 4. It includes a means 35 for closing the ports 33 and 34 when the switchable means 32 is in the second position. The means 35 for closing the ports 33 and 34 includes a means 36 for applying a bias force to close the ports. In the preferred device, the bias force is applied by lip 37 which acts through cylindrical member 38 to press contact members (bosses) 40 and 41 into collar 42.

The valve means 16 also is a means for venting the breath from the passive breather 11 to atmosphere. The venting is via ports 44A, 44B, 44C, and 44D best seen in FIGS. 1 and 6. Another important aspect of the invention is that the valve chamber 46 also acts as a spin separator trap 46 for trapping the moisture in the breath from the active breather. The invention also provides a means 47 for preventing the trapped moisture from dropping from the spin separator trap into the breathing organs 23, 24 of the passive breather. This means 47 includes the structure of the valve member 26 and the means for applying 14 which places the openings 28 significantly outside of the circumference of opening 88.

Figure 7:
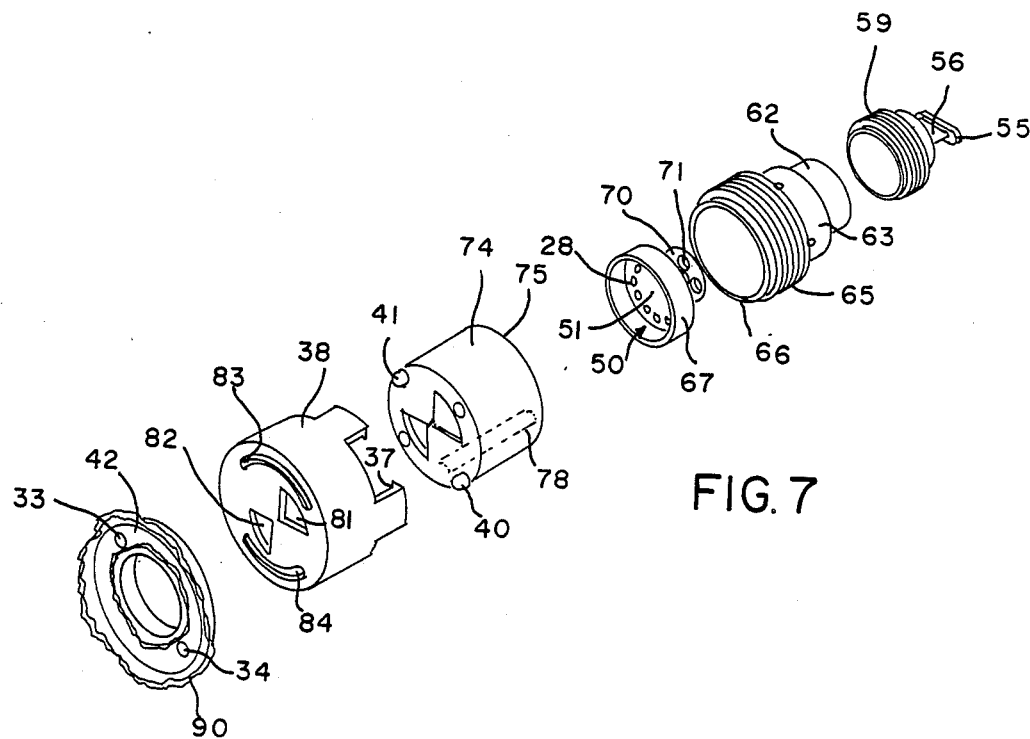
FIG. 7 is an exploded, perspective view of the resuscitation device with the inflation means partially cut away.

Another important aspect of the invention is the means 50 (FIG. 7) for preventing regurgitation from the passive breather from entering the valve chamber 46. In the preferred embodiment this comprises a screen 51, the small openings 28 of which screen the regurgitation from the valve chamber 46. Another important aspect is that means 90 for guiding the breath from housing 53 to the distal end 92 of the device, which end defines an area sufficiently large to cover one or more breathing organs 23, 24 of the passive breather, is inflatable; a further aspect is that when not inflated the member 90 is foldable back over the housing 53.

Turning now to a more detailed description of the preferred embodiment of the invention, the mouthpiece 18 includes an oval mouth plate 55 at one end of a flattened portion 56, and a cylindrical portion 57 at the other end, the flattened and cylindrical portions smoothly joined by a sloping portion 58, the cylindrical portion having three circumferential ribs 59, all of which are formed in a single molded piece having a hollow interior. The plate 55 and flattened portion 56 are of a size that will comfortably fit an average person's mouth.

Valve means 16 preferably comprises an upper cylindrical cup-shaped portion 62 molded bottom to bottom with a lower cylindrical cup-shaped portion 63. The two portions 62 and 63 have a circular opening 27 between them and the lower portion 63 has four circumferential molded ribs 65, four circular openings 44A–44D, and a groove 66 along the exterior wall of the cup perpendicular to and cutting through the ribs 65. Valve means 16 also includes valve member 26 which comprises cylindrical cup-shaped portion 67 having a ring of small holes 28 about the outer perimeter of the cup "bottom". In the center of the exterior of the "bottom" of the cup is a circular raised area 68 having a sloping shoulder 30 and a cylindrical extension 69 with a disk-shaped member 70 at its distal end. Member 70 has four openings 71 through it and a sloping shoulder 72. The valve means 16 is manufactured by molding the back-to-back cup portion separate from the valve member 26, then assembling the two by pressing disk member 70 through the opening 27.

The means for applying 14 preferably comprises switchable means 32 and inflatable means 22. The switchable means is best seen in FIGS. 3 and 4. It preferably comprises a first cylindrical member 74, a second cylindrical member 38, and collar 42. The cylindrical member 74 is preferably molded in the form of a cylindrical cup having wedge-shaped openings 76 and 77 and protruding bosses 40 and 41 formed in the bottom of the cup, a raised rib 78 (FIG. 7) along the inner wall of the cup parallel to the axis of the cup, and openings 79 and 80. Second cylindrical member 38 preferably is molded in the form of a cylindrical cup with two wedge-shaped openings 81 and 82 in the bottom of the cup, two slots 83 and 84 along a chord of a circle about the axis of the cup bottom, and four extension members, such as 86, each member 86 having a lip 37 extending inward from the inner rim of the extension. Collar 42 is molded in the form of a disk with a central circular opening 88 and two circular openings (ports) 33 and 34. Collar 42 also forms part of the inflatable means 22 and opening 88 is part of the opening 20. Wedge-shaped openings 77, 78 and 81, 82 form the opening 29 when they are aligned.

Inflatable means 22 includes collar 42 and inflatable bladder 90. Bladder 90 is shaped in the form of a frustrum of a cone when inflated with the smaller end 91 of the frustrum being attached to the collar 42, and thus proximal to the valve means 16, and the larger end of the frustrum 92 being distal to the valve means 16. The shape and dimension of the bladder is such that, when it is not inflated, the distal end 92 and the major portion of the bladder 90 is foldable back over the proximal end 91 and the relatively rigid housing of the switchable means 32 and valve means 16, as shown in FIG. 2, so that the whole forms a compact unit that can be easily carried in an ordinary-sized pocket in the clothes of nurses or other emergency personnel.

Inflatable means 22 is preferably molded out of silicon rubber. Liquid silicon rubber is poured into a female mold shaped in the form of the exterior of the bladder 90. Then a male mold shaped like the interior of the bladder 90 is inserted into the female mold. The molds are heated to cure the silicon rubber bladder 90, then the silicon rubber collar 42 is added and the juncture is heated to fuse the collar to the bladder. The other portions of the device are preferably injection molded out of Tyril™ plastic available from Dow Chemical Corporation, Midland, Mich.

The outer diameter of ribs 59 and the inner diameter of cup 62 are such that the mouthpiece 18 makes a tight frictional fit in cup 62. Likewise the outer diameter of ribs 65 and the inner diameter of cylinder 74 are such that the cup 63 makes a tight frictional fit in cylinder 74. Rib 78 in cylinder 74 slides into groove 66 in cup 63 and ribs 65 which interlocks the two so cylinder 74 can be turned within cylinder 38 by holding the outer part of cylinder 38 in one hand and cup 62 in the other. Collar 42 is attached to cylinder 38 using a conventional rubber cement or two-part epoxy. Cylinders 74 and 38 are molded separately, then, after collar 42 is attached to cylinder 38, cylinder 74 is placed over cylinder 38 and popped into place by applying pressure. The thinness of extension members, such as 86, permits them to flex to allow the insertion of cylinder 74.

In the preferred embodiment, plate 55 is about 0.650 inches long by 0.250 inches wide by 0.100 inches thick. Mouthpiece portion 56 is about 0.500 inches by 0.205 inches by 0.500 inches long. Cylindrical portion 57 is about 0.783 inches in diameter, with ribs 59 about 0.861 inches in diameter and 0.050 inches wide. Valve means upper cup 62 is about 0.862 inches in inner diameter and about 0.650 inches long while the lower cup 63 is about 1.235 inches in inner diameter and about 0.850 inches long, with ribs 65 of about 1.389 inches in diameter and 0.050 inches wide. Valve member 26 is about 1.232 inches in outer diameter and 0.305 inches in length. Raised area 68 is about 0.420 inches in diameter and 0.050 inches high. Extension 69 is about 0.120 inches in diameter by 0.160 inches high. Disk 70 is about 0.050 inches thick by 0.042 inches in diameter. Cylinder 74 is about 0.525 inches long and has an inner diameter of about 1.390 inches and an outer diameter of about 1.470 inches, while bosses 40 and 41 are about 0.190 inches high and 0.199 inches in diameter. Cylinder 38 is about 1.500 inches in inner diameter and 0.600 inches in length from the top of lip 37 to the bottom surface. Lip 37 extends about 0.035 inches beyond the rim. Extensions 86 are about 0.300 inches wide and extend about 0.175 inches beyond the main body of the cylinder. Collar 42 is about 1.580 inches in diameter by 0.210 inches Bladder 90 is about 0.012 inches thick. The critical wall thicknesses for functioning purposes are given above or can be determined from the data given above. The walls of the other pieceparts, including the means for receiving 12, the valve means 16 parts, and cylinders 74 and 38 are Preferably between about 0.035 and 0.050 inches thick. Openings 71 are about 0.110 inches in diameter, opening 27 is about 0.400 inches in diameter, openings 28 are about 0.100 inches in diameter, openings 44A-44D are about 0.109 inches in diameter, opening 88 is about 0.850 inches in diameter, while ports 79, 80, 33, and 34 are about 0.194 inches in diameter. Slots 83 and 84 are about 0.210 inches wide by 90 degrees of arc with a 0.105 inch radius formed at each end. Wedge shaped openings 76, 77, 81, and 82 are each defined by taking a 0.0167 inch slice out of each of the two sides of a wedge of about 0.45 degrees of arc by 0.850 inches in radius. The intersection of the slices "removed" from the wedges creates the central island 96 separating the points of the wedges. The slope of lip 37, shoulder 30, and shoulder 72 are each about 45 degrees. Rib 78 is a half cylinder of about 0.085 inches in diameter by 0.485 inches long while groove 66 is about 0.100 inches in diameter by 0.400 inches long.

Figure 6:
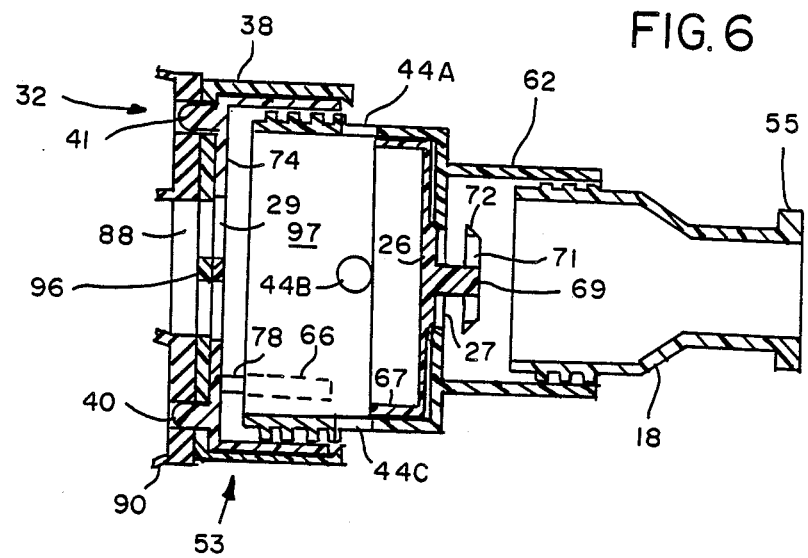
FIG. 6 is a cross section of the device of FIG. 5 with the one-way valve in the exhaust position and the inflation means partially cut away.

The invention is operated by inserting the mouthpiece 18 into the valve means 16 and valve means 16 into cylinder 74 with Rib 78 sliding int groove 66 and seating to prevent the cylinder 63 from going all the way to the bottom of cylinder 74. The switchable means 32 is placed in the first position in which ports 80 and 33 and 79 and 34 align by grasping the body of the valve means 16 with one hand and the means for applying 14 with the other and twisting counter-clockwise as far as it will go easily. The bladder 90 is then inflated by blowing into mouthpiece 18, which moves valve member 26 downwards if it was not already in that position. When the bladder is fully inflated, the valve means 16 is twisted clockwise with respect to the means for applying 14 until it clicks as bosses 40 and 41 slip into ports 33 and 34 respectively. The distal end 92 of the bladder 90 of the resuscitation device is then placed over the nose and mouth of the person to be resuscitated (after checking the tongue etc. according to proper CPR procedures) and the pliable distal end 92 forms a seal about the breathing organs to sealably engage the opening 20 to the breathing organs. The active breather then blows breath into the mouthpiece 18. The breath passes through opening 20 to resuscitate the passive breather. After a full breath through the mouthpiece 18, the active breather releases the air pressure to permit the passive breather to exhale (and assists the exhale in accordance with CPR procedures). The exhaled breath forces valve member 26. upwards opening exhausts ports 44A-44D and seating shoulder 30 about the periphery of opening 27 sealing the opening as shown in FIG. 6. Ports 44A-44D direct the exhaled breath away from the active breather The entire device can also be lifted off the face of the passive breather during exhale, if desired.

A feature of the invention is that as the breath from the active breather flows through the valve means 16 it must turn at a right angle to move from opening 27 to openings 28, and then must turn again to pass through the openings 28. These two turns "spin" the breath causing the heavier moisture particles in the breath to separate from the air. Thus the chamber 46 is a "spin separator" trap. In this disclosure a spin separator trap is defined as a chamber or other structure that forces all of the breath passing from one breather to another to turn. The air again must turn as it moves from openings 28 to opening 29, and thus the chamber 97 is a second spin separator trap which further removes moisture from the breath. Moisture from the spin separator trap. 46 may pass through openings 28 if the device is used for long periods. The second spin separator trap 97 prevents this moisture from passing through opening 20 to the passive breather. Looked at another way, since the device is generally used in the vertical position shown in FIG. 1, the moisture will tend to drop toward the passive breather. The offset of openings 28 from openings 29 and 88 prevents this moisture from dropping through openings 29 and 88 into the breathing organs of the passive breather.

Another feature of the invention is that the small size of holes 28 and the fact that valve member 26 closely abuts the upper surface of the valve chamber 46, prevents regurgitation and other fluid from the passive breather from entering the valve chamber 46. The valve member 26 thus acts as a screen to screen the regurgitation form the valve chamber 46. This prevents the fluid from working its way through the chamber on subsequent breaths from which it could work its way to the mouthpiece 18. The fluid will instead tend remain in chamber 97 or to exit through ports 44A-44D with the exhaust breath since these ports are slightly larger then openings 28 and are fully vented to the atmosphere. The transparent plastic of the device allows the active breather to see if the regurgitation and other fluid becomes significant, so that it can be cleared from the device and the breathing passages of the passive breather.

It is a further feature of the invention that the vertical distance from the top rim 75 of cylinder 74 to the tip of contact means (bosses) 40, 41 is more than the vertical distance from the lower edge of lip 37 to the upper surface 94 of collar 42. Thus, bosses 40, 41 press into collar 42 which is flexible, being made of silicon rubber. This creates a bias force between the collar 42 and lip 37. Thus when bosses 40 and 41 are slid into ports 33 and 34, they pop into the ports and close them firmly. It is noted that although collar 42 is relatively flexible as compared with the rigidity of the plastic bosses 40 and 41, it is relatively rigid with respect to the thin bladder 90.

Another feature of the invention is that the means 90 for guiding the breath from the valve-sized housing 53 to the area defined by distal end 92 is inflatable. It is noted that the valve mechanisms of person-to-person resuscitation devices are of a similar size of the neighborhood of about one-half inches to two inches in diameter since the valve must be large enough to easily pass sufficient breath under the force available but small enough to respond satisfactorily to the breathing forces. At the same time the area necessary to cover the normal human mouth and nose is of a larger size, about three to six inches in diameter. The prior art that has used mask-like structures to apply the breath to the passive breather has uniformly used rigid cones or shapes similar to cones to guide the breath from the smaller valve housing to the larger area where the apparatus is applied to the breathing organs. The inflatable means 90 for guiding the breath permits the resuscitation device of the invention to be significantly more compact. A further feature is that the inflatable bladder 90 is designed so that when deflated it folds back over the housing 53. This further enhances the compactness.

A final important feature of the invention is its small size. The resuscitation device according to the invention is compact enough to fit into an ordinary-sized clothes pocket, which is defined herein as being of the size of a trousers side pocket, a relatively uniformly sized pocket with which everyone is familiar. Thus the device is compact enough to fit into the typical pockets in the uniforms of nurses, medics, and other emergency personnel. Its small size makes it more apt to be placed in these pockets and many other areas, such as first aid kits, hospital trays, bedside drawers, and other such places where it can be immediately available when needed.

A novel person-to-person resuscitation device that protects both the person being resuscitated and the person doing the resuscitation from exchange of bodily fluids that may cause disease, is very compact, and has numerous other advantages has been described. It is evident that those skilled in the art may now make many changes in the device as described without departing from the inventive concepts. For example, the bladder may be rolled, or folded against flange 42, etc. and still be very compact. The dimensions and relative placement of parts may be varied. Some features may be eliminated and additional features may be added. Equivalent materials may be used. Thus the invention should be construed as embracing each and every novel feature and combination of features present in and possessed by the invention described.

What is claimed is:

1. A person-to-person resuscitation device comprising:
    means for receiving breath from an active breather;
    means for applying breath to a passive breather; and
    valve means for permitting breath to pass from said means for receiving to said means for applying and for preventing fluid from passing from said means for applying to said means for receiving;
    said means for applying having an opening therein and including an inflatable bladder and a relatively rigid collar, said collar encircling said opening, supporting said bladder about said opening, and having one or more inflation ports in it; and
    said device further comprising a switchable means switchable from a first position to a second position for directing said breath through said one or more inflation ports to inflate said bladder when in said first position and for directing said breath to said passive breather through said opening in said second position.

2. The resuscitation device of claim 1 wherein said switchable means is part of said means for applying.

3. The resuscitation device of claim 1, wherein said switchable means comprises means for closing said one or more inflation ports when said switchable means is in said second position.

4. The resuscitation device of claim 3 wherein said one or more ports comprises a circular hole in said collar and said means for closing comprises a rounded boss having a diameter equal to or greater than the diameter of said hole.

5. The resuscitation device of claim 3 wherein said means for closing includes means applying a bias force for closing said one or more inflation ports.

6. The resuscitation device of claim 5 wherein said collar comprises a resilient material and said means applying a bias force comprises a first hollow cylindrical member and a second hollow cylindrical member, said cylindrical members nested together so that the outer circumference of one cylindrical member abuts the inner circumference of the other cylindrical member, a contact member connected to said first cylindrical member, in contact with said collar, and engageable with said ports, said second cylindrical member attached to said collar and having a lip extending over the rim of said first cylindrical member opposite said collar, and the relative distances between said collar and said lip and said collar and said ring of said first cylindrical member being such that said lip presses against said rim and forces said contact member to compress said collar to provide said bias force.

7. The resuscitation device of claim 1 wherein said device is sufficiently compact to fit into an ordinary-sized clothes pocket.

* * * * *